US008926632B2

(12) United States Patent  
Mahaffey et al.

(10) Patent No.: US 8,926,632 B2  
(45) Date of Patent: Jan. 6, 2015

(54) DERMATOME SWIVEL DOUBLE ACTING VALVE

(75) Inventors: Mark Mahaffey, New Philadelphia, OH (US); Bruce Straslicka, Medina, OH (US)

(73) Assignee: Zimmer Surgical, Inc., Dover, OH (US)

( * ) Notice: Subject to any disclaimer, the term of this patent is extended or adjusted under 35 U.S.C. 154(b) by 636 days.

(21) Appl. No.: 13/155,433

(22) Filed: Jun. 8, 2011

(65) Prior Publication Data  
US 2012/0316576 A1  Dec. 13, 2012

(51) Int. Cl.  
*A61B 17/322* (2006.01)  
*A61B 17/00* (2006.01)  
*A61B 19/00* (2006.01)

(52) U.S. Cl.  
CPC ..... *A61B 17/322* (2013.01); *A61B 2017/00544* (2013.01); *A61B 2019/4868* (2013.01)  
USPC ........................................................ 606/132

(58) Field of Classification Search  
USPC ............................ 606/132, 133; 137/613, 594  
See application file for complete search history.

(56) References Cited

U.S. PATENT DOCUMENTS

| | | | |
|---|---|---|---|
| 3,128,079 A | 4/1964 | De Groff | |
| 3,820,543 A * | 6/1974 | Vanjushin et al. | 606/132 |
| 3,857,178 A | 12/1974 | Stevens | |
| 3,890,704 A | 6/1975 | Ferraro et al. | |
| 3,934,591 A | 1/1976 | Gleason | |
| 4,038,986 A | 8/1977 | Mahler | |
| 4,098,278 A | 7/1978 | Schwartz | |
| 4,270,540 A | 6/1981 | Schwartz | |
| 4,281,681 A | 8/1981 | Teague | |
| 4,413,645 A * | 11/1983 | Seabase et al. | 137/223 |
| 4,690,139 A | 9/1987 | Rosenberg | |
| 4,748,003 A | 5/1988 | Riley | |
| 4,754,756 A | 7/1988 | Shelanski | |
| 4,838,284 A | 6/1989 | Shelanski | |
| 4,917,086 A | 4/1990 | Feltovich | |
| D322,672 S | 12/1991 | Feltovich et al. | |
| 5,443,801 A | 8/1995 | Langford | |
| D401,340 S | 11/1998 | Waldman et al. | |
| 5,873,881 A | 2/1999 | McEwen et al. | |
| 5,921,980 A | 7/1999 | Kim | |
| 6,080,166 A | 6/2000 | McEwen et al. | |
| 6,139,554 A * | 10/2000 | Karkar et al. | 606/131 |
| 6,520,976 B1 | 2/2003 | Gage | |
| 6,530,931 B1 | 3/2003 | Rosenberg | |
| 6,622,753 B2 * | 9/2003 | Thordarson et al. | 137/613 |

(Continued)

FOREIGN PATENT DOCUMENTS

GB    774 689 A     5/1957  
GB    1 605 003 A  12/1981

*Primary Examiner* — Thomas McEvoy  
*Assistant Examiner* — Julie A Szpira  
(74) *Attorney, Agent, or Firm* — Seager, Tufte & Wickhem, LLC

(57) ABSTRACT

A dermatome having a handle and an attachment including a valve, where the valve may include a first bobbin at least partially defining a first flow path and a second flow path, a second bobbin at least partially defining a first flow path, an inlet port at least partially defined by the second bobbin and an outlet port at least partially defined by the first bobbin. The ports of the valve may open in response to an application of a mechanical act to the attachment and the ports may close in response to the absence or removal of the mechanical act.

24 Claims, 12 Drawing Sheets

(56) References Cited

U.S. PATENT DOCUMENTS

| | | | |
|---|---|---|---|
| 6,799,605 B1* | 10/2004 | Van Scyoc et al. | 137/614.03 |
| 6,923,821 B2 | 8/2005 | Wortrich | |
| 2002/0029812 A1* | 3/2002 | Hotta et al. | 137/613 |
| 2004/0225309 A1 | 11/2004 | Eriksson et al. | |
| 2008/0115848 A1* | 5/2008 | Bruck et al. | 137/613 |
| 2008/0236687 A1* | 10/2008 | Kadow et al. | 137/614.03 |
| 2009/0138027 A1 | 5/2009 | Lucas et al. | |
| 2009/0157095 A1 | 6/2009 | Barker et al. | |
| 2009/0157096 A1 | 6/2009 | Boles | |

* cited by examiner

DERMATOME SWIVEL DOUBLE ACTING VALVE

TECHNICAL FIELD

The disclosure is directed to dermatomes for surgically harvesting grafts of skin. More particularly, the disclosure is directed to dermatome valve assemblies.

BACKGROUND

Conventional dermatomes are used for cutting skin tissue to obtain transplantable skin grafts. A skin graft is a patch of healthy skin that is harvested from one area of the body or donor site to cover a damaged or skinless area of the body. Typically, a dermatome has a front end holding a flat blade to be placed in contact with a tissue surface and a motor to oscillate the blade from side to side to create a slicing action which cuts the tissue as the dermatome is moved along the tissue surface.

SUMMARY

The disclosure is directed to several alternative or complementary designs, materials and methods of using medical device structures and assemblies. Although it is noted that conventional dermatomes exist, there exists a need for improvement on those devices.

Accordingly, one illustrative embodiment may include a dermatome having a handle extending from a cutting head and a valve or attachment system connected to the handle. The attachment or valve system may include a first bobbin that at least partially defines a first flow path and a second flow path, and a second bobbin in adjustable communication with the first bobbin that also at least partially defines the first flow path. The first bobbin may at least partially define an outlet port, where the outlet port communicates with an outlet flow through the second flow path. In addition, the second bobbin may at least partially define an inlet port, where the inlet port communicates with an inlet flow through the first flow path. The ports may operate to open the paths in response to an application of a mechanical act to the valve or attachment system and the ports may operate to close the paths in response to the removal or absence of the mechanical act.

The above summary of some example aspects is not intended to describe each disclosed embodiment or every implementation of the claimed disclosure.

BRIEF DESCRIPTION OF THE DRAWINGS

The disclosure may be more completely understood in consideration of the following detailed description of various embodiments in connection with the accompanying drawings, in which.

Figure 1:
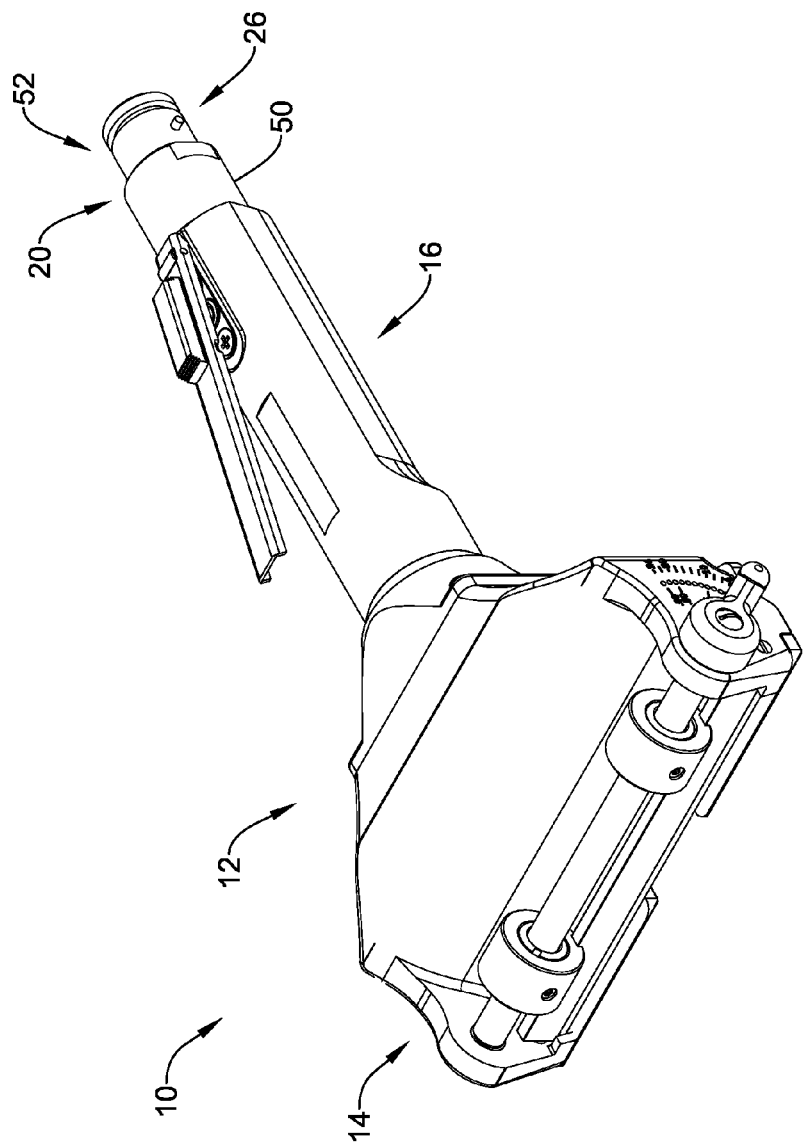
FIG. 1 is a top perspective view of a dermatome according to an aspect of the disclosure.

While the disclosure is amenable to various modifications and alternative forms, specifics thereof have been shown by way of example in the drawings and will be described in detail. It should be understood, however, that the intention is not to limit aspects of the claimed disclosure to the particular embodiments described. On the contrary, the intention is to cover all modifications, equivalents, and alternatives falling within the spirit and scope of the claimed disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the claimed disclosure. The illustrative embodiments depicted are intended only as exemplary. Selected features of any illustrative embodiment may be incorporated into an additional embodiment unless clearly stated to the contrary.

Figure 2:
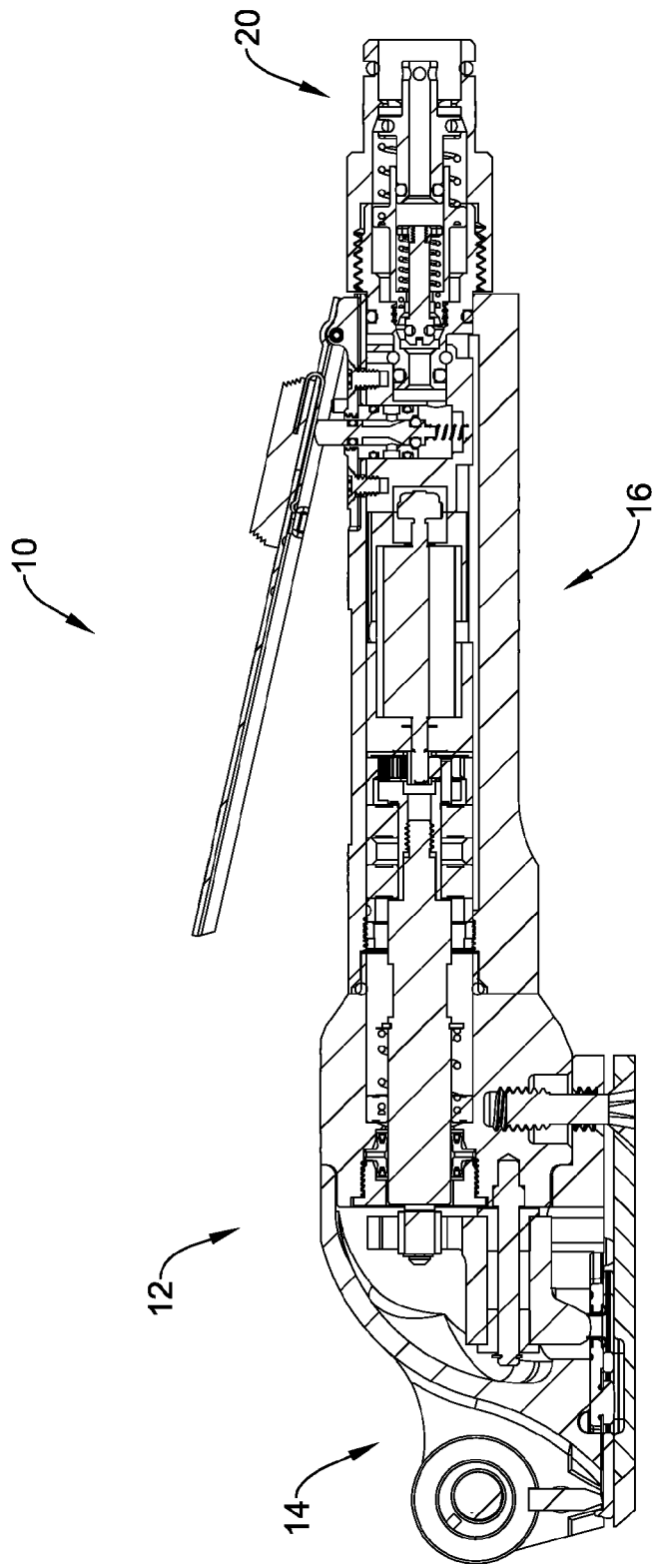
FIG. 2 is a cross-sectional view of a dermatome according to an aspect of the disclosure.
Figure 9:
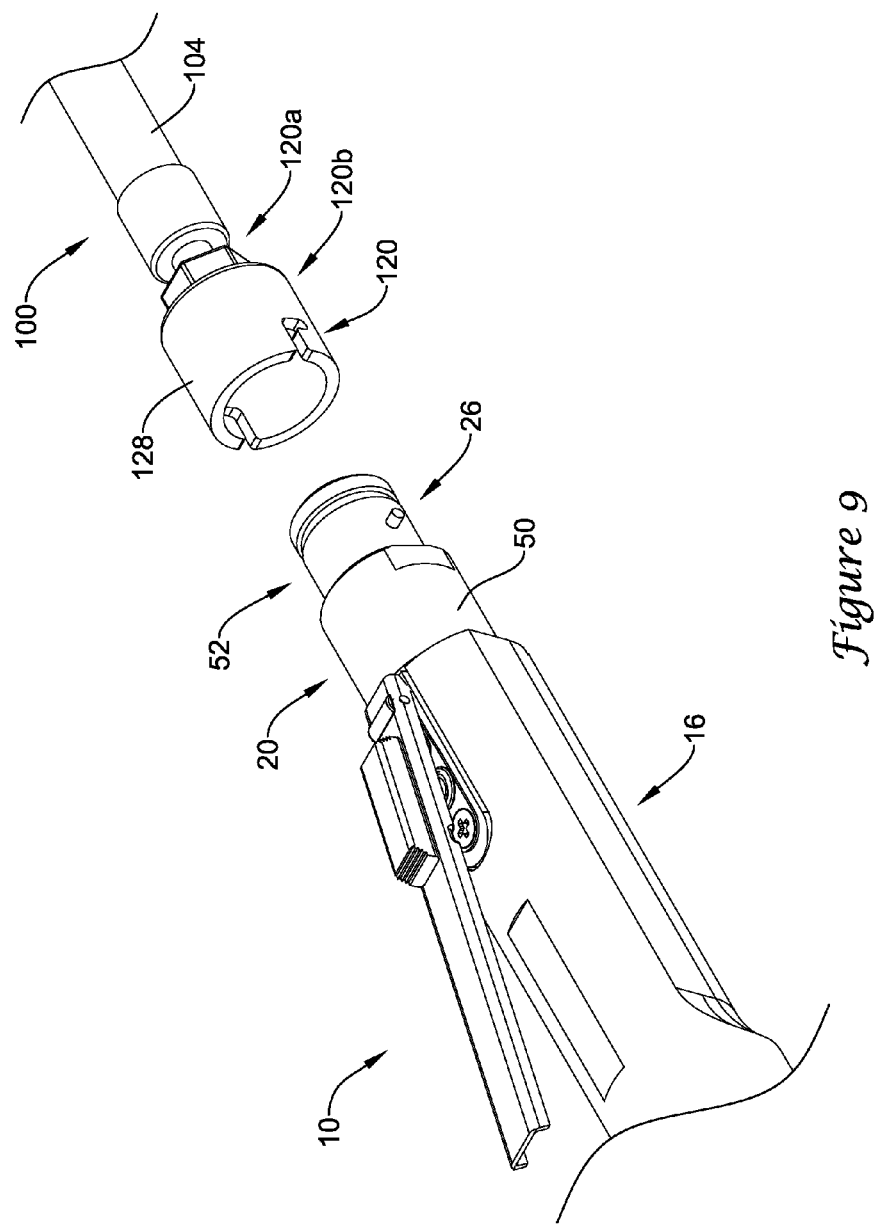
FIG. 9 is a partial perspective view of a dermatome and a hose according to an aspect of the disclosure.

Referring to FIGS. 1, 2 and 9, a dermatome 10 for harvesting grafts of skin tissue has a main body 12, with a head 14 (e.g., a cutting head) connected to a handle 16. Dermatome 10 may include a valve or an attachment 20 extending from handle 16 and configured to connect to a fluid hose 100 capable of providing a pressurized fluid to a fluid motor (not shown) of a dermatome 10, as well as an exhaust pathway extending from the motor of the dermatome 10 away from a sterile field of the surgical procedure within which dermatome 10 may be used.

As seen in FIGS. 2-8D, valve or attachment 20 may include a system for opening (i.e., unobstructing) and closing (i.e., obstructing) fluid flow paths into and out of handle 16. The valve system 20 may include a first bobbin 30, a second bobbin 40, an inlet port 60 at least partially defined by second bobbin 40 and an outlet port 62 at least partially defined by first bobbin 30. The system of attachment 20 may further include a first flow path 22 at least partially defined by first bobbin 30 (e.g., by an inner surface of a passage through first bobbin 30) and second bobbin 40 (e.g., between an outer surface of second bobbin 40 and an inner surface of receiver 90) and a second flow path 24 at least partially defined by first bobbin 30 (e.g., between an outer surface of first bobbin 30 and an inner surface of casing 50) and receiver 90 (e.g., between an outer surface of receiver 90 and an inner surface of casing 50). To either open and unobstruct or close and obstruct paths 22, 24, inlet port 60 and outlet port 62 may be opened or closed, respectively, by a single operation on the structure of attachment 20. In operation, attachment 20 may allow fluid to enter an interior of a dermatome to interact with a fluid motor driving the cutting blade when inlet port 60 and outlet port 62 are open for the purpose of powering the dermatome or for any other purpose, such as driving the cutting blade. Further, attachment 20 may operate to prevent fluid from entering an interior of main body 12 of dermatome 10 when inlet port 60 and outlet port 62 are closed.

Figure 3:
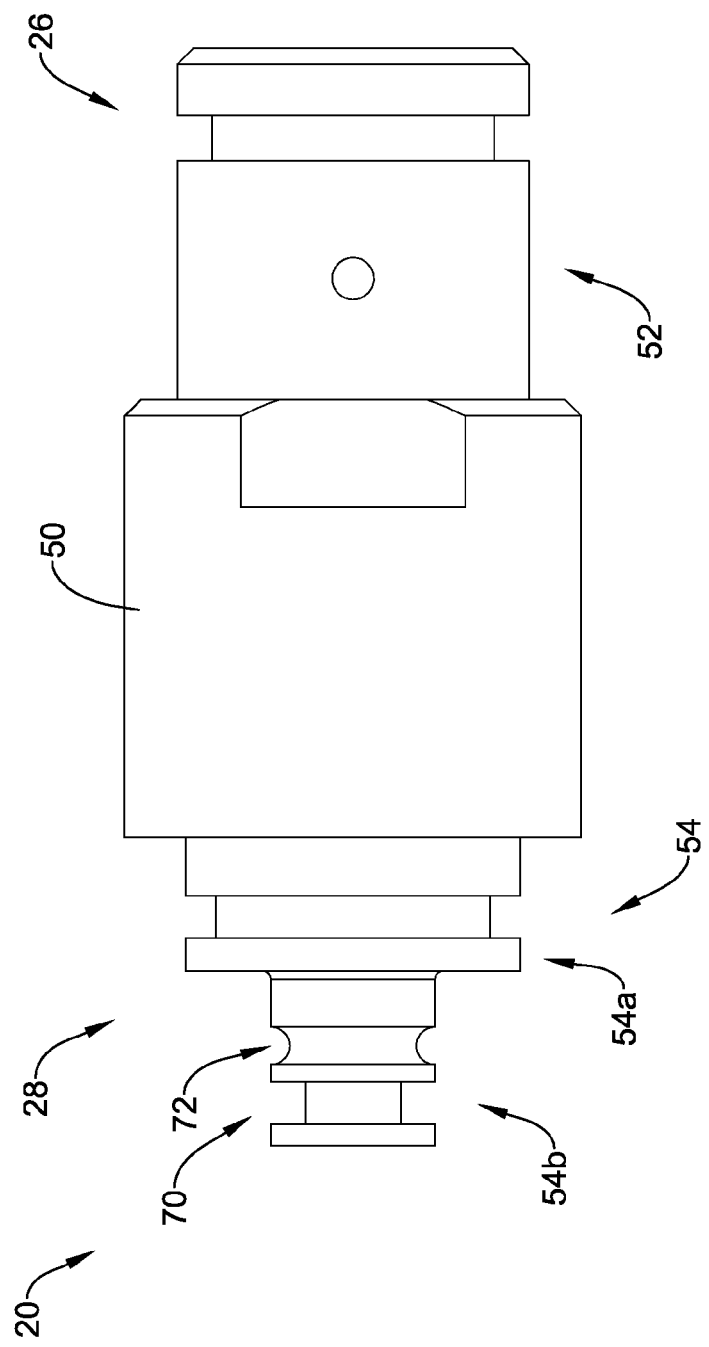
FIG. 3 is a side view of a dermatome attachment according to an aspect of the disclosure.

FIG. 3 depicts a side view of attachment 20 that shows a housing or casing 50 generally enclosing or surrounding the structure of attachment 20. Casing 50 may be unitarily formed or may comprise two or more pieces interconnected. As shown, casing 50 may include two members threadably coupled together to facilitate assembly of internal components. Casing 50 may take on any shape or size capable of generally enclosing the structure therein and connecting to dermatome handle 16 and fluid hose 100. For example, casing 50 may be generally concentric about the structure therein. A first end 52 of casing 50 may be configured for connection to fluid hose 100. The connection between fluid hose 100 and attachment 20 may be made by any hermetically sealed and releasable connection technique known in the art. For example, the connection between hose 100 and attachment 20 may be made using o-rings 18 and bearings or a bayonet locking system (as depicted in FIG. 9).

A second end 54 of casing 50 may be configured to connect to handle 16, as seen for example in FIGS. 1 and 2. The connection between attachment 20 and handle 16 may be made by any hermetically sealed and releasable connection technique known in the art. For example, the connection between attachment 20 and handle 16 may be made using o-rings 18 and bearings so as to allow handle 16 to swivel with respect to attachment 20. In other embodiments, attachment 20 may be permanently secured to handle 16.

Figure 4:
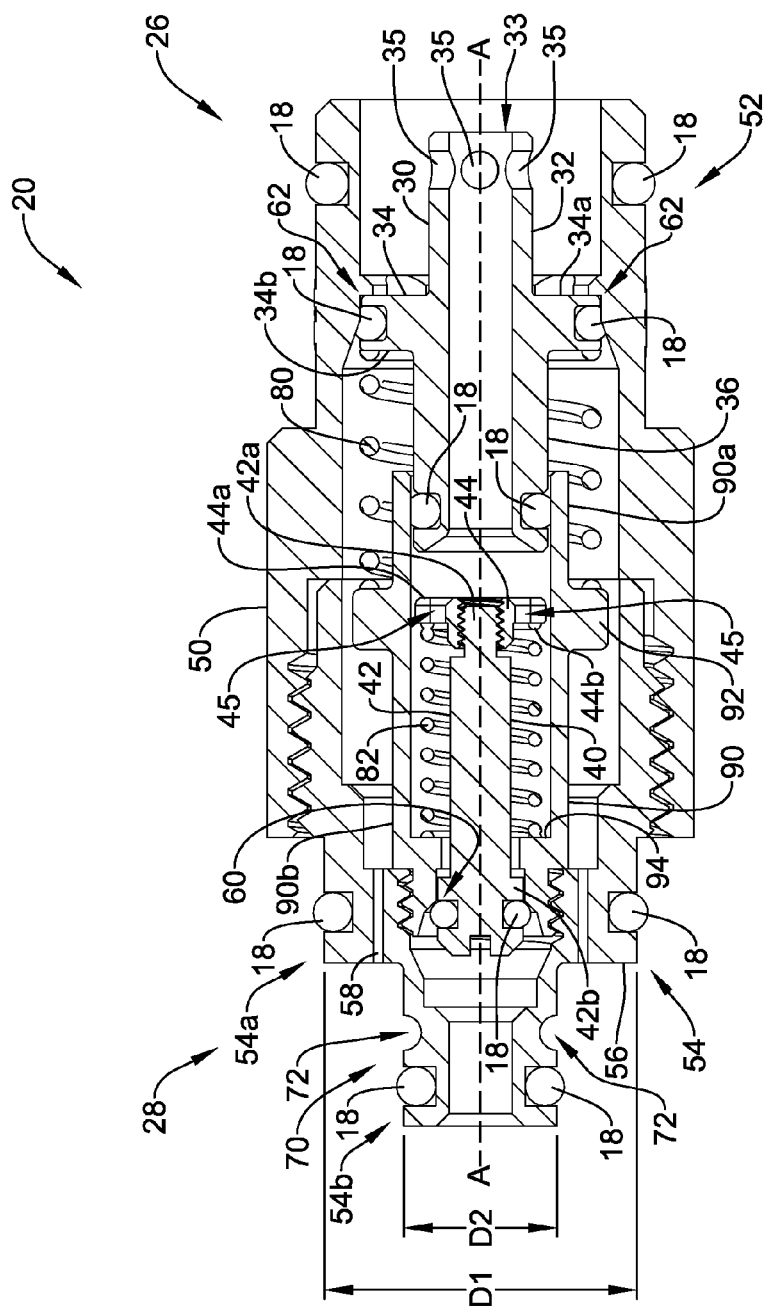
FIG. 4 is a cross-sectional view of a dermatome attachment while the attachment is in a closed position.
Figure 5:
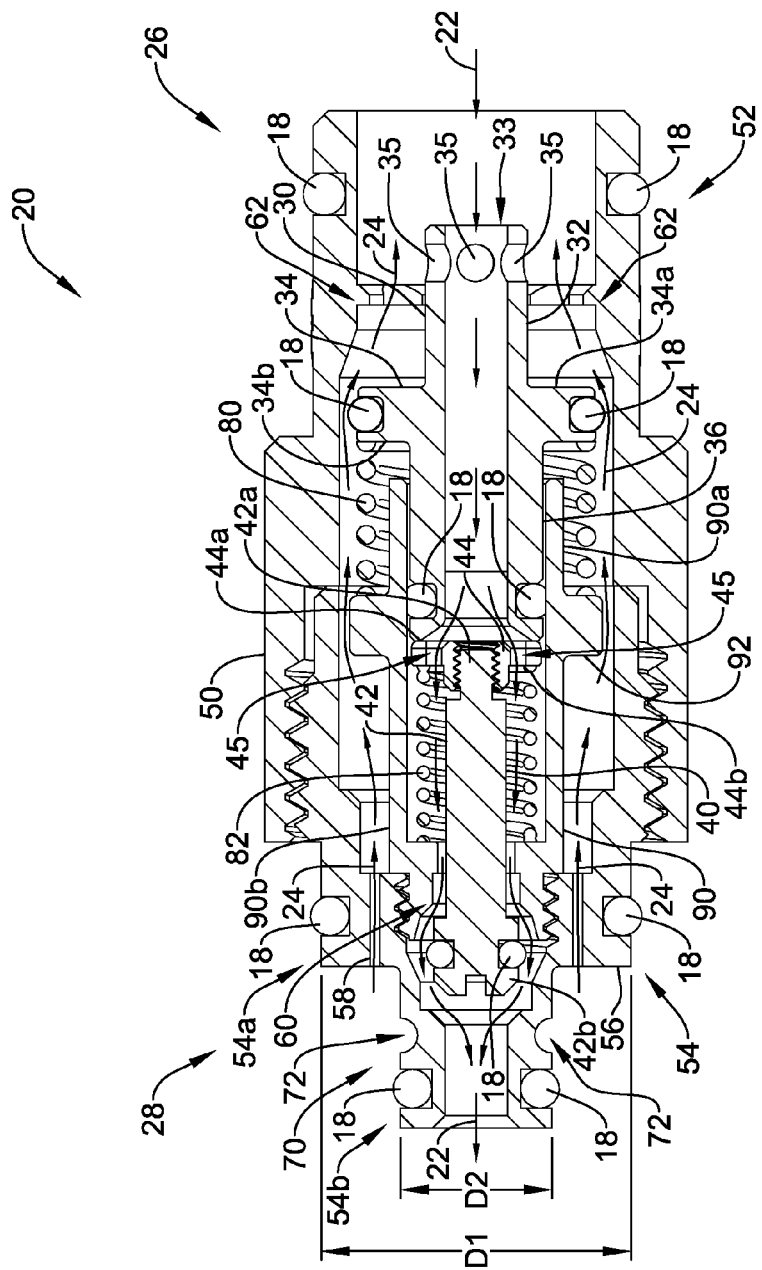
FIG. 5 is a cross-sectional view of a dermatome attachment with directional arrows indicating flows flowing through the aspect of the disclosure depicted in FIG. 4, while the attachment is in an open position.

FIG. 4 depicts portions of the interior structure of attachment 20 within casing 50. The interior structure may be generally concentric about a centered axis A-A extending through attachment 20 from a hose connecting end 26 to a handle connecting end 28 in an elongated direction of attachment 20. The structure may include first bobbin 30 and second bobbin 40, along with a first spring 80, a second spring 82 and an aerator or bobbin receiver 90. Within casing 50, bobbin receiver 90 may receive first bobbin 30 and second bobbin 40, where first bobbin 30 may extend through a first end 90a of bobbin receiver 90 and second bobbin 40 may extend through a second end 90b of bobbin receiver 90. Further, in an exemplary aspect, first spring 80 may surround the first end 90a of bobbin receiver 90 and extend between first bobbin 30 and an exterior step 92 positioned between a first end 90a and a second end 90b of bobbin receiver 90, while second spring 82 may be placed within second end 90b of bobbin receiver 90 and extend between second bobbin 40 and an interior step 94 of receiver 90. As a result of the connections, first flow path 22 may be defined by at least a hollow interior of first bobbin 30, an interior of bobbin receiver 90 and an exterior of second bobbin 40, as seen in FIG. 5. As also shown in FIG. 5, second flow path 24 may be an annular flow path concentric to first flow path 22 and may be defined by at least the structure of an interior of casing 50, an exterior of first bobbin 30 and an exterior of bobbin receiver 90. In addition, second bobbin 40 and bobbin receiver 90 may form inlet port 60 and first bobbin 30 and casing 50 may form outlet port 62.

Inlet port 60 may include an o-ring 18, or other mechanism capable of creating a hermetic seal, on either second bobbin 40 or bobbin receiver 90, or both, so as to provide the fluid tight seal when inlet port 60 is closed. Similarly, outlet port 62 may include an o-ring 18 or other mechanism capable of creating a hermetic seal on either first bobbin 30 or casing 50, or both, so as to provide the fluid tight seal when outlet port 62 is closed. In an exemplary aspect seen in at least FIGS. 4 and 5, o-rings 18 may be placed on second bobbin 40 and first bobbin 30, respectively, to provide the seal when ports 60, 62 are closed.

First bobbin 30 may be configured and located within casing 50, so as to be capable of receiving and engaging a pressurized fluid hose 100 or a fitting 120 thereof. As seen in FIGS. 4 and 5, first bobbin 30 may be unitarily formed and may have an elongated first end 32 extending generally from a front face 34a of an extension 34 and an elongated second end 36 extending generally from a back face 34b of extension 34. As seen in FIGS. 4 and 5, extension 34 may be a medial flange portion of first bobbin 30. Although first bobbin 30 may be unitarily formed, it may alternatively be formed of two or more pieces configured to connect to one another. In addition, first bobbin 30 may have a substantially hollow interior extending therethrough, as seen in FIGS. 4 and 5, where the hollow interior may be configured to at least partially define first flow path 22.

Elongated first end 32 of first bobbin 30 may have an open terminal end 33 configured to abut a ball of a ball valve 122 located within a pressurized fluid hose 100. Between terminal end 33 and extension 34, elongated first end 32 may comprise at least one opening 35 configured to receive a pressurized fluid via an inner lumen 106 accessed through the opening of the ball valve 122 within fluid hose 100. Fluid from hose 100 may enter opening(s) 35 and flow through the interior of first bobbin 30 and follow first flow path 22. Extension 34 may include a front face 34a and a back face 34b, where front face 34a may be configured to engage casing 50 when in a closed position and back face 34b may be configured to engage first spring 80, as shown in FIG. 4, with first spring 80 surrounding elongated second end 36. Extension 34 and casing 50 may form outlet port 62 and may work together to block second flow path 24 when extension 34 is in a closed position. Extension 34 or casing 50, or both, may include a seal (e.g., an o-ring 18) to create a hermetic seal at outlet port 62. Elongated second end 36 of first bobbin 30 may extend to and within bobbin receiver 90. Elongated second end 36 may directly abut an interior of bobbin receiver 90 or may include a seal (e.g., an o-ring 18) to create a hermetic connection between second end 36 and receiver 90, or both. Second end 36 may slide within receiver 90 in response to a mechanical act applied to first bobbin 30 at front face 34a, or terminal end 33 or at another location. As second end 36 slides within receiver 90, back face 34b may act upon first spring 80 and second end 36 may contact and act on second bobbin 40.

Second bobbin 40 may be a unitary piece or comprise more than a single piece where the pieces are releasably connected. For example, as seen in FIGS. 4 and 5, second bobbin 40 may be made of a stem 42 and a stem nut 44 threadably engaging stem 42. Stem nut 44 may engage stem 42 at a first end 42a, as shown in FIGS. 4 and 5, or at any other location along stem 42. Stem nut 44 may include a first side 44a and a second side 44b, with fluid ports 45 extending from first side 44a to second side 44b. Fluid ports 45 may be discrete fluid ports, such as channels or flutes, placed concentrically, or otherwise, about stem 42 or fluid ports 45 may be a single hole extending annularly around stem 42. Second side 44b may abut second spring 82, where spring 82 may surround stem 42 of second bobbin 40 and extend from second side 44b to an interior step 94 of receiver 90. A second end 42b of stem 42 may be located adjacent a second end 90b of receiver 90 to form inlet port 60. Second end 90b of receiver 90 or second end 42b of stem 42, or both, may include a seal (e.g., o-ring 18) for providing a hermetic seal of inlet port 60 when attachment 20 is in a closed position. Thus, when attachment 20 is in a closed position, second end 42b may engage receiver 90 to close inlet port 60 and block first flow path 22. When in an open position, second end 42b and receiver 90 may separate to open inlet port 60 and allow fluid to flow therethrough along first flow path 22.

Figure 6:
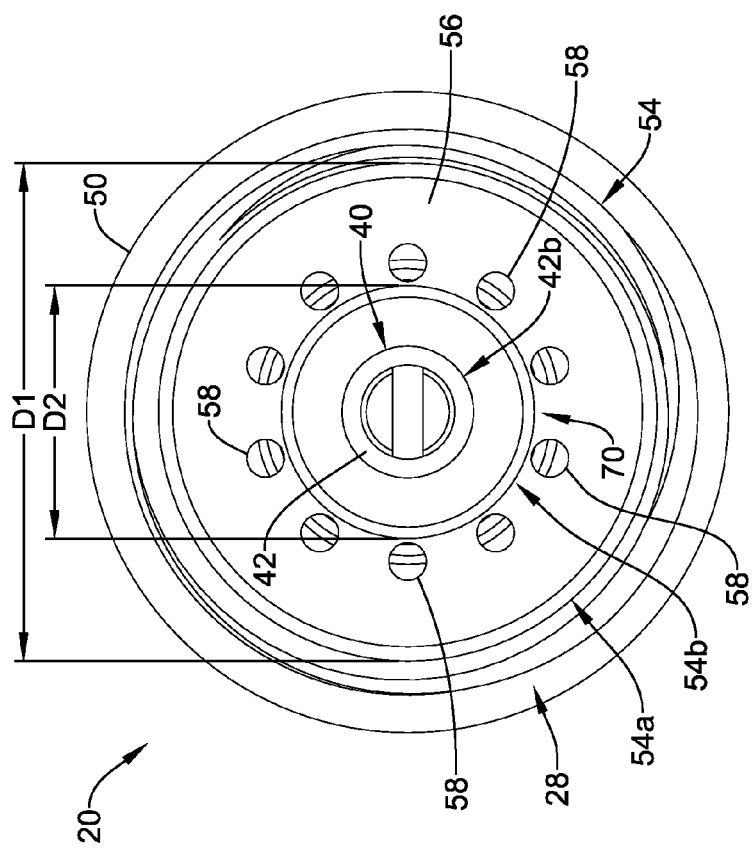
FIG. 6 is an end view of FIG. 3 of the end of an aspect of the dermatome attachment configured to connect to a handle of the dermatome.
Figure 7:
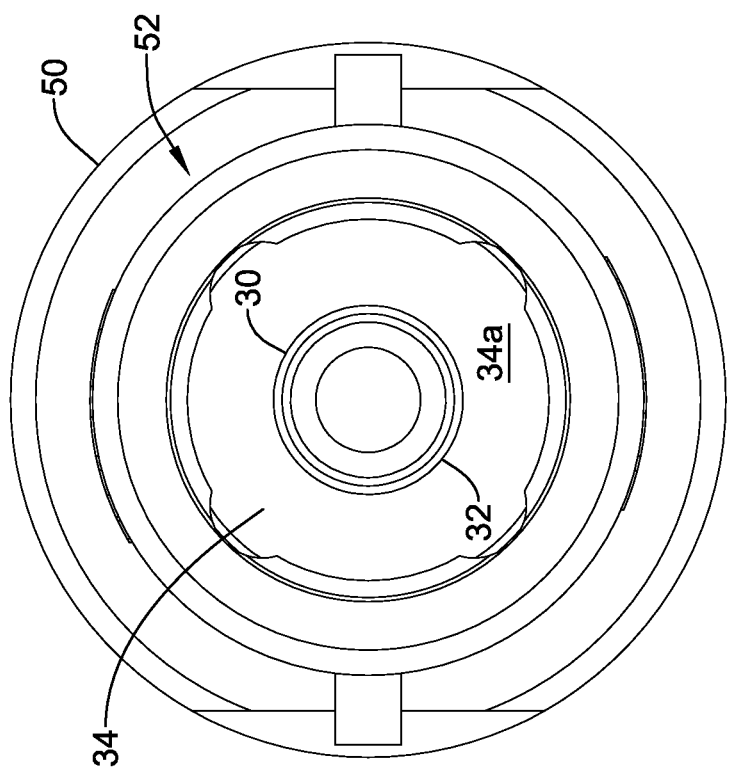
FIG. 7 is an end view of FIG. 3 of the end of an aspect of the dermatome attachment configured to connect to a fluid hose, where the end is an end opposite the end depicted in FIG. 6.

As seen in FIGS. 3-6, second end 54 of casing 50 located at a handle connecting end 28 of attachment 20 may have a first portion 54a with a diameter D1 and a second portion 54b with a diameter D2, where diameter D2 may be smaller than diameter D1. An exhaust plate 56 may extend from diameter D2 to diameter D1 and may include exhaust holes 58, as shown in FIG. 6, configured to receive fluid flowing through second flow path 24 and exhausted from the fluid motor. Exhaust holes 58 may take on any shape or size located within plate 56. Plate 56 may be unitarily formed as part of casing 50 or may be a plate added to bridge a gap between first portion 54a and second portion 54b, for instance.

Second portion 54b may form neck 70 and handle 16 may be configured to engage attachment 20 at neck 70 and first portion 54a. Handle 16 may engage neck 70 and first portion 54a in any manner creating a releasable hermetic seal at the engagements. For example, the hermetic seals may be made through the use of o-rings 18 and those o-rings 18 may circumscribe first portion 54a and second portion 54b or may be placed within an interior lumen (not shown) and annular lumen (not shown) of handle 16, or a combination thereof. Further, the interior lumen of handle 16 may connect to attachment 20 at neck 70 in any manner that allows for handle 16 to swivel with respect to attachment 20. For example, neck 70 may include at least one indentation 72 at one or more locations (axially or circumferentially, or both, displaced at more than one location) around the outer circumference of neck 70 for the purpose of receiving ball bearings or other connectors from handle 16. Alternatively or in addition, neck 70 may comprise ball bearings that engage handle 16. Further, indentation 72 may be an indented concentric ring around the circumference of neck 70, as shown for example in FIGS. 3-5, or any other indented shape.

An exemplary first end 52 of casing 50 located at a hose connecting end 26 of attachment 20 is depicted in FIGS. 3-5 and 7. First end 52 may be configured for connection to a fluid or air hose 100. The connection may be made through any connection technique desired. For example, a hose 100 may be connected to first end 52 through a bayonet lock, complementary threading, or any other releasable connecting technique known in the art. In addition, first end 52 may include one or more seals (e.g., an o-ring 18) for providing a hermetic seal between first end 52 and hose 100. Alternatively, or in addition, hose 100 may include seals for providing the hermetic seal between first end 52 and hose 100.

Different stages of an exemplary engagement between hose 100 and attachment 20 are seen in FIGS. 8A-8D. FIGS. 8A-8D depict hose 100 comprised of a fitting 120 engaged with an inner tubular member 102 and an outer tubular member 104, where fitting 120 may be used for making a connection with attachment 20. Fitting 120 may comprise a first end 120a and a second end 120b and may include a ball valve 122 located within or proximate second end 120b. First end 120a may be configured for connection to inner tubular member 102 and outer tubular member 104 through any known connection technique. For example, the connection may be facilitated with a glue substance or through a pressure fitting, such as crimping or other technique. Further, first end 120a may have channels 124 extending from first end 120a to second end 120b for the purpose of passing exhaust fluid to an annular lumen 108 of hose 100 or for any other purpose. Second end 120b may comprise an inner fitting portion 126 and an outer fitting portion 128. Inner fitting portion 126 may be configured to engage first bobbin 30 and provide a hermetic seal therebetween. The seal may be provided by, for example, one or more o-rings 18 circumferentially arranged around first bobbin 30 or within inner fitting portion 126 or both. Ball valve 122 may be located within inner fitting portion 126 and may be activated (e.g., lifted off a valve seat) in response to interacting with terminal end 33 of first bobbin 30 or may be activated in another manner. Outer fitting portion 128 of fitting 120 may engage an exterior of casing 50, as seen for example in FIGS. 8B-8D, or another portion of casing 50 exterior of second flow path 24. Such engagement may include providing a hermetic seal between casing 50 and outer fitting portion 128, where the hermetic seal may be provided by, for example, either outer fitting portion 128 or casing 50 including an o-ring 18, or a combination thereof.

Figure 8A:
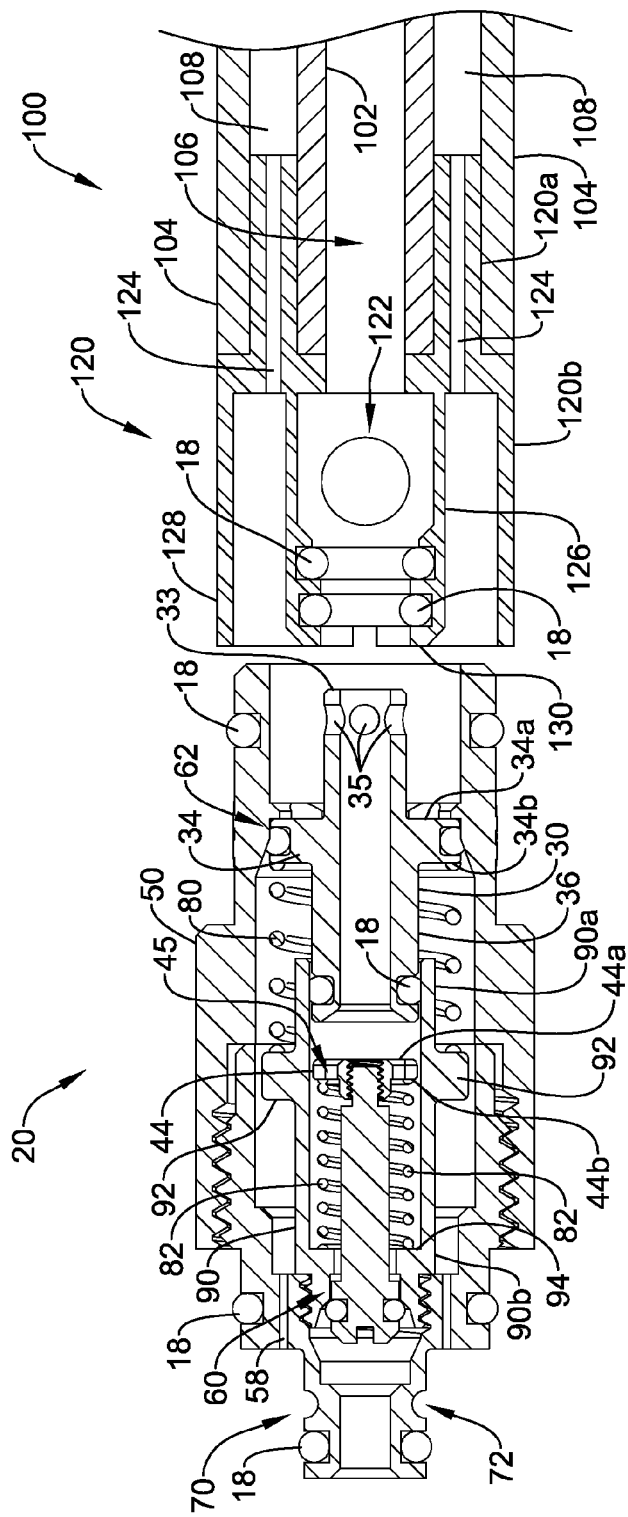
FIGS. 8A-8D are side cross-sectional views of a dermatome according to an aspect of the disclosure, where the dermatome is in different stages of connecting to an exemplary fluid hose in each figured iteration.
Figure 8B:
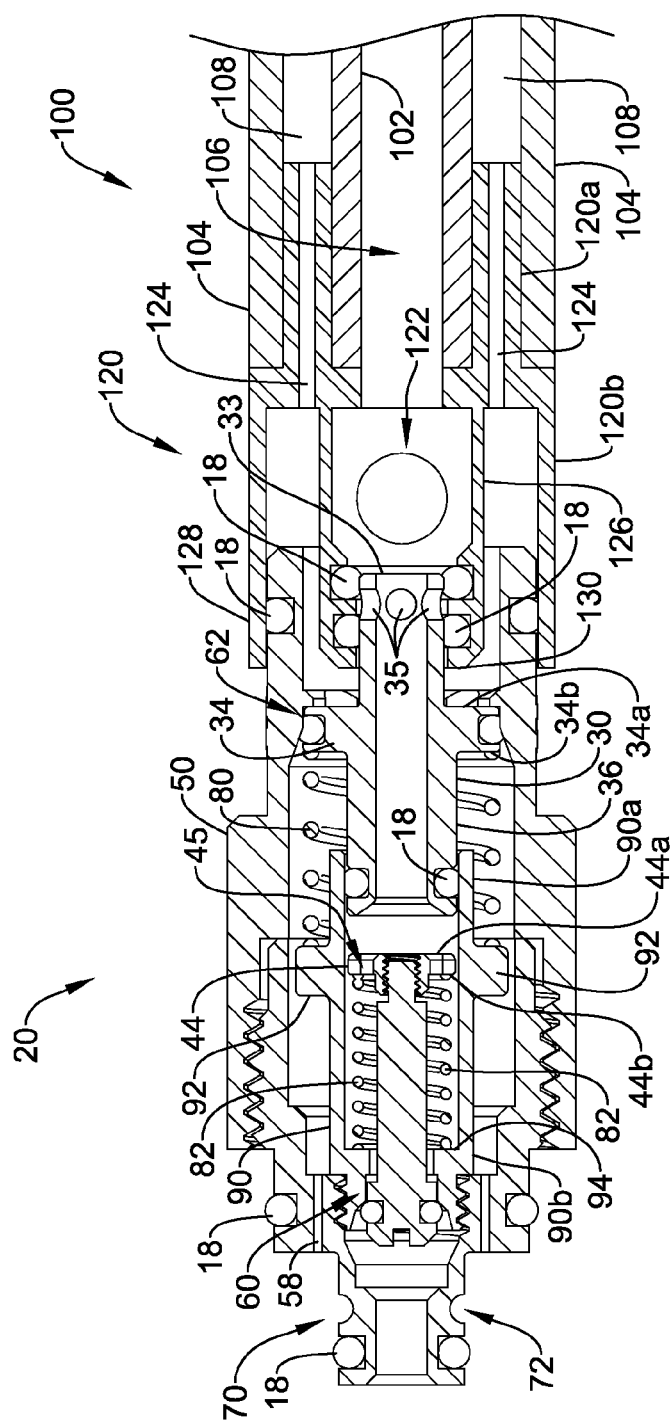
Figure 8C:
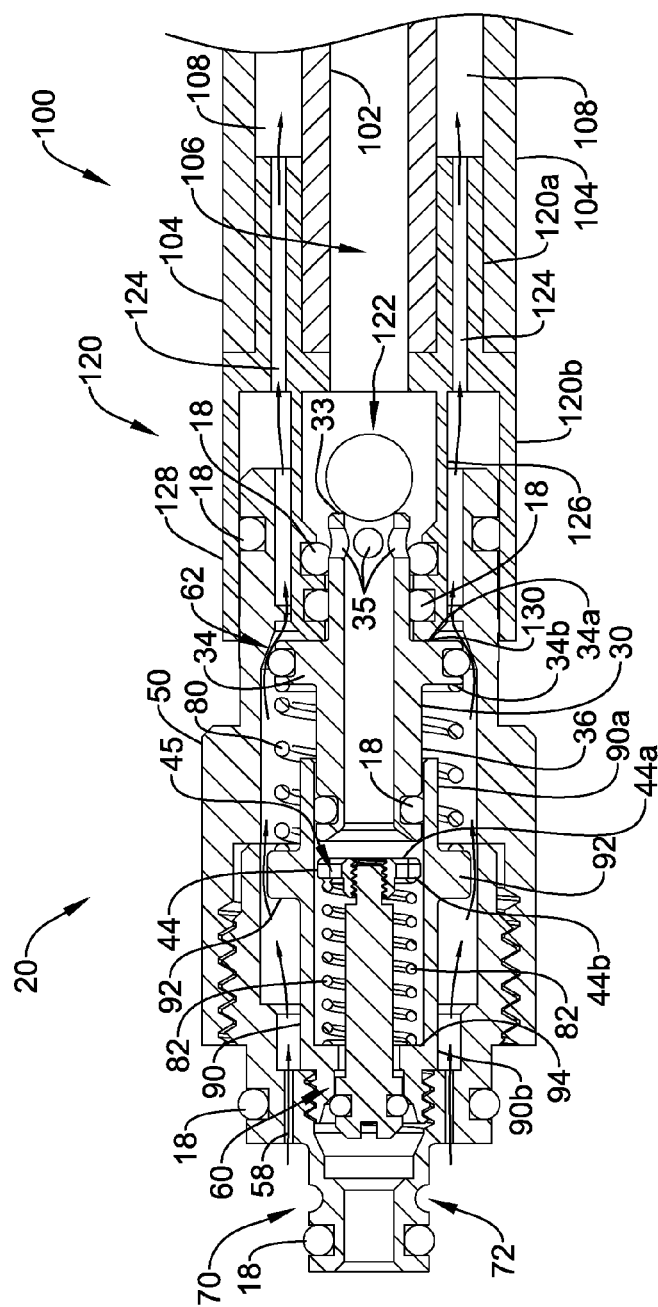

In FIG. 8B, attachment 20 is depicted in a closed position and hose 100 has begun engagement with attachment 20, where second end 120b of fitting 120 has initially engaged casing 50 and first bobbin 30. FIG. 8C shows further engagement between attachment 20 and hose 100, where terminal end 33 of first bobbin 30 abuts ball valve 122 and begins to allow fluid to flow from hose 100 through openings 35 of elongated first end 32 of first bobbin 30. At the same time or at a proximate time, a terminal end 130 of inner fitting portion 126 may engage front face 34a of first bobbin 30 and place a force thereon sufficient to overcome the force of first spring 80 to move first bobbin 30 to open outlet port 62. It is noted that when outlet port 62 is initially opened, first bobbin 30 may not yet have moved into engagement with stem nut 44 of second bobbin 40 to open inlet port 60.

Figure 8D:
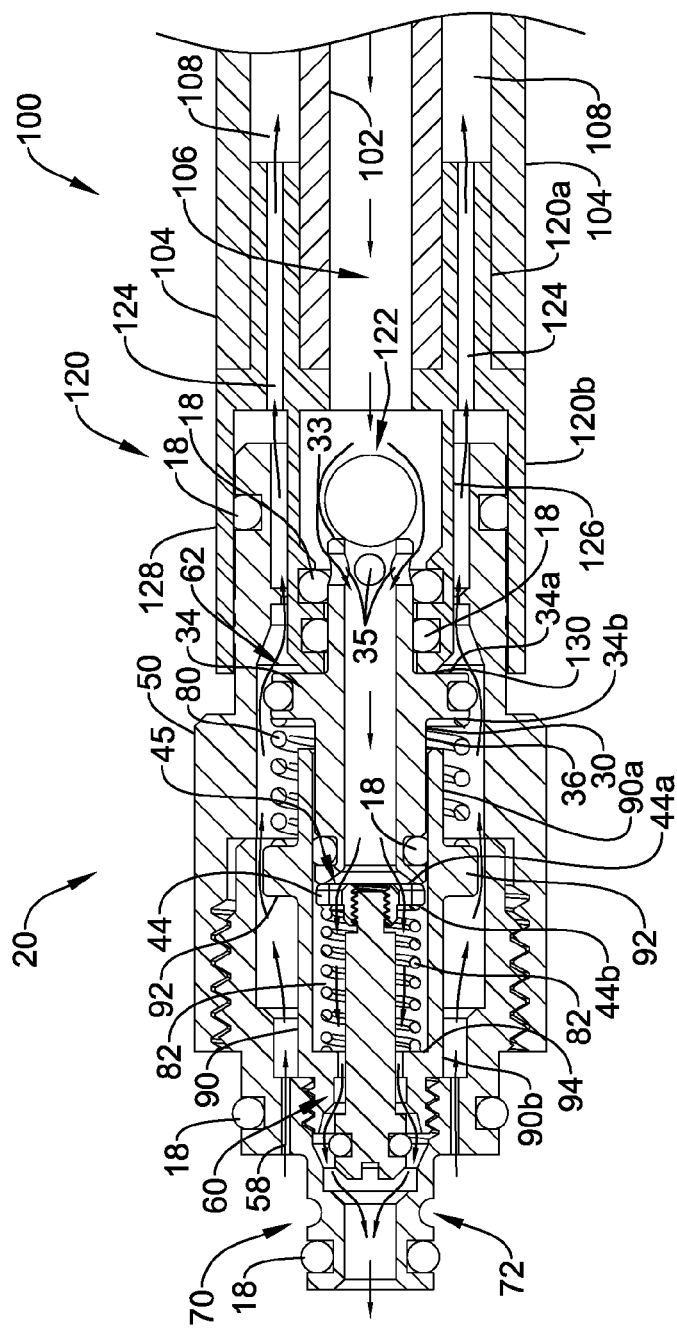

FIG. 8D depicts full engagement of hose 100 with attachment 20, where first bobbin 30 has been displaced a requisite amount by the connection between hose 100 and attachment 20 to open inlet port 60 along with outlet port 62. Inlet port 60 may open in response to first bobbin 30 contacting, and applying a force on, first side 44a of stem nut 44 of second bobbin 40, where the applied force overcomes the force of second spring 82 to activate and move second bobbin 40. Thus, a fully attached hose 100 opens the valves of attachment 20 allowing fluid to flow from an inner lumen 106 of hose 100 through first flow path 22 within attachment 20 to fluid motor (not shown), and then exhaust fluid from the fluid motor to and through second flow path 24 to annular lumen 108 of hose 100 via channels 124 in fitting 120.

Although FIGS. 8A-D depict the attachment of hose 100 to attachment 20 as an iterative process, the attachment may be achieved in one or more fluid steps, where, for example, a force from fitting 120 engaging attachment 20 overcomes a biasing force of springs 80, 82 and in response to the force, first bobbin 30 moves a sufficient distance to engage and press against second bobbin 40 to move second bobbin 40. This exemplary process ensures an outlet flow path may be opened prior to opening an inlet flow path.

Applying or connecting a hose 100 to attachment 20 may include the application of a single mechanical act to attachment 20; for example, the mechanical act may be the placing of a force or pressure greater than a threshold pressure or force on first bobbin 30 through terminal end 130 of inner fitting portion 126, or other portion of fitting 120 or hose 100, where the threshold pressure or force is a sufficient pressure or force to overcome a biasing force of springs 80, 82. The single mechanical act may be solely the application or connection of a hose 100 to attachment 20 or the connection of a hose 100 to attachment 20 such that fluid from hose 100 communicates with first flow path 22 or simply the application of a pressurized fluid against the first bobbin 30, or other mechanical act. Alternatively or in addition, an act acting on attachment 20 may include an electrical signal or other type of act or signal.

During the application of the single mechanical act, outlet port 62 may be opened prior to inlet port 60 opening, as seen from FIGS. 8B-8D, or ports 60, 62 may be opened simultaneously in response to the presence of the single mechanical act. In one example, the mechanical act may be the application of at least a threshold pressure of thirty-two (32) pounds per square inch (psi) or ~2.2 bars of pressure, or any other desired pressure or force level, to front face 34a and terminal end 33 of first bobbin 30. In other instances, the threshold pressure may be set to sixteen (16) psi or more, twenty (20) psi or more, twenty-four (24) psi or more, twenty-eight (28) psi or more or thirty-six (36) psi or more or another desired amount of pressure or force. The amount of pressure applied to first bobbin 30 may be any pressure proportional to a combined or effective spring constant of first and second springs 80, 82. An exemplary effective spring constant would have enough pressure to keep inlet and outlet ports 60, 62 closed during washing and sterilization of dermatome 10. Further, in response to the absence or removal of the single mechanical act, ports 60, 62 may be closed and may remain closed until a further application of the mechanical act.

After or prior to using the above described system in an operation or other event utilizing a dermatome 10, it may be desirable to wash or sterilize dermatome 10. It has been realized that it is advantageous to prevent washing or sterilizing materials from entering the interior of dermatome 10. Such prevention of unwanted material within dermatome 10 during washing and sterilizing may be achieved by keeping inlet and outlet ports 60, 62 of attachment 20 in a closed position throughout the washing process. A closed position may be achieved, automatically or otherwise, by removing the application of the single mechanical act (e.g., removal of the applied force from the hose connection or other external pressure source) to attachment 20. Once the single mechanical act is absent, springs 80, 82 act on bobbins 30, 40 to close inner and outer ports 60, 62, respectively, which essentially may block first and second flow paths 22, 24. Such blockage, in addition to other hermetic seals of the system, will prevent unwanted materials from entering dermatome 10 and interacting with the fluid motor (not shown) and other interior parts of dermatome 10 throughout the washing or sterilization process. Accordingly, with hose 100 decoupled from attachment 20 of dermatome 10, inlet and outlet ports 60, 62 may be automatically closed such that dermatome 10 is ready to be washed or sterilized. Thereafter, dermatome 10 may be washed or sterilized without permitting fluids from the washing/sterilization process from entering into the internal components of dermatome and adversely affecting the performance and/or integrity of dermatome 10. Upon completion of the washing/sterilization process, hose 100 may be reattached to attachment 20 of dermatome 10 for use in a medical procedure.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A dermatome comprising:
   a handle extending from a cutting head; and
   a valve connected to the handle, the valve including:
   a first bobbin having a medial flange portion and at least partially defining a first flow path and a second flow path;
   a second bobbin in adjustable communication with the first bobbin and at least partially defining the first flow path;
   an inlet port at least partially defined by the second bobbin, the inlet port communicating with an inlet flow through the first flow path; and
   an outlet port at least partially defined by the first bobbin, the outlet port communicating with an outlet flow through the second flow path; and
   wherein in response to an application of a mechanical act to the valve, the first flow path is automatically opened at the inlet port and the second flow path is automatically opened at the outlet port; and
   wherein in response to an absence of the mechanical act, the first flow path is automatically closed at the inlet port and the second flow path is automatically closed at the outlet port.

2. The dermatome of claim 1, wherein the first bobbin has a hollow interior partially defining the first flow path, and the first bobbin has an exterior surface at least partially defining the second flow path.

3. The dermatome of claim 2, wherein the second bobbin includes a first seal at the inlet port, and
   wherein the first bobbin includes a second seal at the outlet port.

4. The dermatome of claim 3, further comprising:
   a bobbin receiver at least partially defining the first flow path and the second flow path and at least partially encircling the first bobbin and the second bobbin;
   wherein the first bobbin adjustably communicates with an interior of the bobbin receiver; and
   wherein the first seal engages the bobbin receiver at the inlet port to obstruct the inlet flow through the first flow path in response to the absence of the mechanical act.

5. The dermatome of claim 4, wherein the bobbin receiver comprises an interior step and an exterior step;
   a first spring operationally extending between the exterior step and the medial flange portion of the first bobbin; and
   a second spring operationally extending between the second bobbin and the interior step.

6. The dermatome of claim 1, further comprising:
a casing encompassing the first flow path and the second flow path.

7. The dermatome of claim 6, further comprising:
a bobbin receiver at least partially surrounding the first bobbin and the second bobbin;
a first seal abutting the bobbin receiver to close the first flow path at the inlet port; and
a second seal abutting an interior step of the casing to close the second flow path at the outlet port.

8. The dermatome of claim 7, wherein the casing is concentric about the first and second bobbins, and the interior step extends along an interior circumference of the casing.

9. The dermatome of claim 1, wherein the second bobbin includes a stem and a stem nut configured to connect to the stem.

10. The dermatome of claim 1, wherein the application of a mechanical act comprises connecting a hose to the valve.

11. The dermatome of claim 1, wherein the medial flange portion of the first bobbin includes a face, and
wherein the application of a mechanical act comprises applying a pressure to the face, the pressure having a pressure level of at least a threshold pressure level.

12. The dermatome of claim 11, wherein the threshold pressure level is at least thirty-two pounds per square inch.

13. The dermatome of claim 1, wherein the second flow path is concentric about the first flow path.

14. A dermatome comprising:
a main body; and
an attachment for coupling the main body to an air hose, the attachment including:
a fluid inlet path having an inlet seal; and
a fluid exhaust path having an exhaust seal and the fluid exhaust path is concentric about the fluid inlet path; and
wherein the inlet seal and exhaust seal are activated to seal the respective path in response to a single mechanical act acting on the attachment.

15. The dermatome of claim 14, wherein the single mechanical act is lowering a pressure level applied to the attachment below a threshold pressure level.

16. The dermatome of claim 14, wherein the single mechanical act is removal of a hose from communication with the fluid inlet path.

17. The dermatome of claim 14, wherein the fluid inlet path is concentric about a central axis extending in an elongated direction of the attachment.

18. The dermatome of claim 14, further comprising:
a casing having a neck and encompassing the fluid inlet path and the fluid exhaust path; and
wherein the neck of the casing provides for a swivel connection to a dermatome handle of the main body.

19. The dermatome of claim 18, further comprising:
an indentation located on the neck and concentric to the neck; and
wherein the indentation is configured to provide for the swivel connection to the handle.

20. A dermatome comprising:
a cutting head;
a handle extending from the cutting head;
a first bobbin;
a second bobbin;
a bobbin receiver;
a first spring communicating with the first bobbin and the bobbin receiver; and
a second spring communicating with the second bobbin and the bobbin receiver; and
a casing configured to connect to the handle, and the casing surrounds the first and second bobbins, the bobbin receiver and the first and second springs.

21. The dermatome of claim 20, wherein the bobbin receiver has an exterior and an interior;
wherein the first spring communicates with the first bobbin and the exterior of the bobbin receiver; and
wherein the second spring communicates with the second bobbin and the interior of the bobbin receiver.

22. The dermatome of claim 20, wherein the casing has a swivel location configured to make a swivel connection with the handle.

23. The dermatome of claim 22, wherein the swivel location comprises at least one indentation in the casing; and
wherein one of the at least one indentation is concentric about the casing.

24. The dermatome of claim 22, wherein the casing has a neck configured to engage the handle; and
wherein the swivel location is along an exterior of the neck.

* * * * *